United States Patent
Bae et al.

(10) Patent No.: US 10,577,254 B2
(45) Date of Patent: Mar. 3, 2020

(54) IRON OXIDE NANOPARTICLES DOPED WITH ALKALI METALS OR ALKALI EARTH METALS CAPABLE OF GIGANTIC AC MAGNETIC SELF-HEATING IN BIOCOMPATIBLE AC MAGNETIC FIELD AND METHOD OF PREPARING THE SAME

(71) Applicant: NEO-NANOMEDICS, INC., Blythewood, SC (US)

(72) Inventors: Seong Tae Bae, Seoul (KR); Jung Tak Jang, Seoul (KR)

(73) Assignee: NEO-NANOMEDICS, INC., Blythewood, SC (US)

( * ) Notice: Subject to any disclaimer, the term of this patent is extended or adjusted under 35 U.S.C. 154(b) by 0 days.

(21) Appl. No.: 15/788,782

(22) Filed: Oct. 19, 2017

(65) Prior Publication Data
US 2019/0023584 A1    Jan. 24, 2019

(30) Foreign Application Priority Data
Jul. 21, 2017  (KR) .................. 10-2017-0092955

(51) Int. Cl.
*C01G 49/06* (2006.01)
*A61K 41/00* (2006.01)
(Continued)

(52) U.S. Cl.
CPC .......... *C01G 49/06* (2013.01); *A61K 41/0052* (2013.01); *H01F 1/0045* (2013.01);
(Continued)

(58) Field of Classification Search
None
See application file for complete search history.

(56) References Cited

U.S. PATENT DOCUMENTS

| 5,427,767 A | 6/1995 | Kresse et al. |
| 2005/0090732 A1 | 4/2005 | Ivkov et al. |

(Continued)

FOREIGN PATENT DOCUMENTS

| JP | 2012236778 A | 12/2012 |
| KR | 1020040034224 A | 4/2004 |

(Continued)

OTHER PUBLICATIONS

RS Selvan, K Gokulakrishnan. "Preparation and Characterization of Mg Doped γ-Fe2o3 Prepared by Self-Propagation Method." International Journal of ChemTech Research, vol. 6 No. 3, May-Jun. 2014, pp. 2129-2131. (Year: 2014).*

(Continued)

*Primary Examiner* — Isaac Shomer
(74) *Attorney, Agent, or Firm* — Caesar Rivise, PC

(57) ABSTRACT

Disclosed herein are iron oxide nanoparticles prepared through high-temperature thermal decomposition of an $Fe^{3+}$ precursor and an $M^+$ or $M^{2+}$ (M=Li, Na, K, Mg, and Ca) precursor in an oxygen atmosphere. The iron oxide nanoparticles are nanoparticles, in which an alkali metal or alkali earth metal is doped into an Fe vacancy site of $\gamma-Fe_2O_3$, and generate explosive heat even in a biocompatible low AC magnetic field. Through both in vitro and in vivo tests, it was proven that cancer cells could be killed by performing low-frequency hyperthermia using the iron oxide nanoparticles set forth above.

13 Claims, 12 Drawing Sheets
(12 of 12 Drawing Sheet(s) Filed in Color)

(51) Int. Cl.
 B82Y 5/00 (2011.01)
 B82Y 25/00 (2011.01)
 B82Y 40/00 (2011.01)
 H01F 1/00 (2006.01)
 H01F 1/36 (2006.01)
(52) U.S. Cl.
 CPC .............. *H01F 1/0054* (2013.01); *B82Y 5/00* (2013.01); *B82Y 25/00* (2013.01); *B82Y 40/00* (2013.01); *C01P 2002/52* (2013.01); *C01P 2002/54* (2013.01); *C01P 2002/72* (2013.01); *C01P 2002/80* (2013.01); *C01P 2002/85* (2013.01); *C01P 2004/04* (2013.01); *C01P 2004/64* (2013.01); *C01P 2006/42* (2013.01); *H01F 1/36* (2013.01); *Y10S 977/773* (2013.01); *Y10S 977/811* (2013.01); *Y10S 977/892* (2013.01); *Y10S 977/896* (2013.01); *Y10S 977/915* (2013.01)

(56) References Cited

U.S. PATENT DOCUMENTS

| | | |
|---|---|---|
| 2009/0081122 A1 | 3/2009 | Rufenacht et al. |
| 2011/0256066 A1* | 10/2011 | Bae .................... A61K 41/0052 424/9.32 |
| 2012/0091702 A1 | 4/2012 | Shimizu et al. |
| 2013/0006092 A1* | 1/2013 | Ferrans .............. A61K 41/0028 600/411 |
| 2017/0110228 A1 | 4/2017 | El-Boubbou |

FOREIGN PATENT DOCUMENTS

| | | |
|---|---|---|
| KR | 1020120102572 A | 9/2012 |
| WO | 2015177710 A1 | 11/2015 |

OTHER PUBLICATIONS

PV Adhyapak, V Kadam, U Mahadik, DP Amalnerkar, IS Mulla. "Influence of Li doping on the humidity response of maghemite (γ-Fe2O3) nanopowders synthesized at room temperature." Ceramics International, vol. 39, 2013, pp. 8153-8158. (Year: 2013).*
A-H Lu, El Salabas, F Schuth. "Magnetic Nanoparticles: Synthesis, Protection, Functionalization, and Application." Angewandte Chemie International Edition, vol. 46, 2007, pp. 1222-1244. (Year: 2007).*
M Levy, C Wilhelm, J-M Siaugue, O Homer, J-C Bacri, F Gazeau. "Magnetically induced hyperthermia: size-dependent heating power of γ-Fe2O3 nanoparticles." Journal of Physics: Condensed Matter, vol. 20, 2008, 204133, pp. 1-5. (Year: 2008).*
A Franco Jr., MS Silva. "High temperature magnetic properties of magnesium ferrite nanoparticles." Journal of Applied Physics, vol. 109, 2011, pp. 07B505-1 through 07B505-3. (Year: 2011).*
MMG Saldivar-Ramirez et al. "Study on the efficiency of nanosized magnetite and mixed ferrites in magnetic hyperthermia." Journal of Materials Science: Materials in Medicine, vol. 25, 2014, pp. 2229-2263. (Year: 2014).*
English Translation of JP2012236778A. Obtained from https://patents.google.com/patent/JP012236778A/en?oq=JP2012236778 on Feb. 3, 2020. Originally published in Japanese on Dec. 6, 2012, 5 printed pages. (Year: 2012).*
Bae et al. (2006). Applications of NiFe2O4 nanoparticles for a hyperthermia agent in biomedicine. Applied physics letters, 89(25), 252503:1-3.
International Search Report from corresponding PCT/US2018/015926 dated Apr. 24, 2018.
Jang et al. (2009). Critical enhancements of MRI contrast and hyperthermic effects by dopant-controlled magnetic nanoparticles. Angewandte Chemie International Edition, 48, 1234-1238.
Jeun et al. (2013). Physical parameters to enhance AC magnetically induced heating power of ferrite nanoparticles fo hyperthermia in nanomedicine. IEEE Transactions on Nanotechnology, 12(3), 314-322.
Kim et al. (2012). A new method for the identification and quantification of magnetite-maghemite mixture using conventional X-ray diffraction technique. Talanta, 94, 348-352.
Larumbe et al. (2012). Ni doped Fe3O4 magnetic nanoparticles. Journal of nanoscience and nanotechnology, 12(3), 2652-2660.
LibreTexts. https://chem.libretexts.org/Courses/University_of_Illinois%2C_Springfield/UIS%3A_CHE_267_-_Organic_Chemistry_1_(Morsch)/Chapters/Chapter_06%3A_Understanding_Organic_Reactions/6.08%3A_Kinetics (accessed Aug. 9, 2019).
Liu et al. (2011). Magnetic behavior of Zn-doped Fe3O4 nanoparticles estimated in terms of crystal domain size. The Journal of Physical Chemistry C, 116(1), 134-143.
Ruiz-Baltazar et al. (2015). Effect of the surfactant on the growth and oxidation of iron nanoparticles. Journal of Nanomaterials, 16(1), 202.
Barik et al. (2014) A facile, single-step synthesis of flowery shaped, pure/lithium-doped 3D iron oxides. Journal of Materials Chemistry A, 2, 12380-12389.
Rane et al. (1999). Hydrazine method of synthesis of γ-Fe2O3 useful in ferrites preparation. Part III—study of hydrogen iron oxide phase in γ-Fe2O3. Journal of Materials Science, 10, 121-132.
Selvan et al. (2017). Effect of Doping in Magnetic Character in γ-Fe2O3 Nano Particle. Elixir Applied Chemistry, 103, 45526-45528.
English Abstract for KR 1020040034224 A (2004).
English Abstract for JP 2012236778 A (2012).
Anantharaman et al. (1982). Snythesis & characterisation of doped gamma ferric oxide. Indian Journal of Chemistry, 21A, 714-715.

* cited by examiner

Size ~ 7 nm

IRON OXIDE NANOPARTICLES DOPED WITH ALKALI METALS OR ALKALI EARTH METALS CAPABLE OF GIGANTIC AC MAGNETIC SELF-HEATING IN BIOCOMPATIBLE AC MAGNETIC FIELD AND METHOD OF PREPARING THE SAME

CROSS-REFERENCE TO RELATED APPLICATIONS

This application claims priority from KR 10-2017-0092955, filed Jul. 21, 2017, the contents of which application are incorporated herein by reference in their entireties for all purposes.

BACKGROUND

1. Technical Field

The present invention relates to iron oxide nanoparticles capable of gigantic AC self-heating characteristics in a biocompatible AC magnetic field and application to hyperthermia treatment.

2. Description of the Related Art

Hyperthermia is a cancer treatment modality using characteristics of cancer cells, which are more sensitive to heat than normal cells due to abnormal environments around the cancer cells. This treatment modality maintains the surrounding temperature around the cancer cells in a warm range (41° C. to 45° C.) compared to conventional chemotherapy or radiotherapy, so that this treatment modality has medical advantages in that even extremely small cancer cells localized or deeply seated in living tissue can be selectively killed by heat without damage to normal cells.

Development of AC magnetic self-heating technique in in-vivo environments is required for realizing effective cancer treatment, and recently a great deal of research efforts have been paid to develop AC magnetic self-heating magnetic nanoparticles. In the cancer treatment of hyperthermia using magnetic nanoparticles, the cancer cells were killed by heat generated by magnetic nanoparticles in the AC magnetic field.

In addition, magnetic nanoparticles with superparamagnetism have no aggregation of particle when they are introduced into a living body. When an AC magnetic field is applied to the magnetic nanoparticles, it is possible to easily control heat generated by the applied AC magnetic field and magnetic nanoparticles can be introduced into a living body only by simple injection treatment without a surgery.

Although only bulk sized magnetic materials showed a self-heating effect, there are limitations for their practical application due to difficulty in continuously increasing the self-heating temperature and difficulty in introduction of the magnetic materials into a living body. However, recently, a collaborative research team of the National University of Singapore and the Yokohama National University of Japan has published a study on a new type of self-heating magnetic nanoparticles, and their heating effect in the cells is effective enough for practical application, thus it is possible to expect the realization of a new cancer treatment.

A paper entitled "Applications of $NiFe_2O_4$ nanoparticles for a hyperthermia agent in biomedicine" in Applied Physics Letters, Vol. 89, 252503 (2006) discloses the effectiveness of $NiFe_2O_4$ magnetic nanoparticles as an in vivo hyperthermia agent.

In addition, US Patent Publication No. 2005-0090732 discloses target-oriented hyperthermia treatment using iron oxide. However, most conventional hyperthermia treatment relate to iron oxide nanoparticles showing a heat emission effect at high frequencies and high magnetic field (or high AC magnetic field).

However, in the cancer treatment of high-frequency hyperthermia, red spots may appear around the skin, and area with high fat, some burns, wounds, inflammations, and cell necrosis may occur. Above all, side effects due to harmfulness of high-frequency electric fields to humans are unavoidable. Therefore, this treatment is prohibited for pregnant women, patients with severe inflammation, patients with implanted cardiac pacemakers, and patients with severe pleural effusion and ascites.

In addition, since heat needs to be irradiated to cancer tissues for a long, human bodies are exposed to high-frequency electromagnetic waves for a long time, and thus, there is a problem in that normal tissues can also be damaged.

To solve the aforementioned problems, it is required to develop the magnetic nanoparticles capable of self-heating in a biocompatible low AC magnetic field (or a safe AC magnetic field).

BRIEF SUMMARY

It is an object of the present invention to provide iron oxide nanoparticles capable of sufficient self-heating even in a biocompatible low (or safe) AC magnetic field.

In accordance with one aspect of the present invention, iron oxide nanoparticles are nanoparticles in which $\gamma$-$Fe_2O_3$ (maghemite) is doped with an alkali metal ion or alkali earth metal ion, specifically nanoparticles in which an Fe vacancy site of $\gamma$-$Fe_2O_3$ is doped with an alkali metal ion or alkali earth metal ion.

The alkali metal ion may include lithium (Li), sodium (Na) and potassium (K), and the alkali earth metal ion may include magnesium (Mg) or calcium (Ca).

The doping metal ion may include at least one alkali metal ion or alkali earth metal ion, preferably at least one selected from the group consisting of $Li^+$, $Na^+$, $K^+$, $Mg^{2+}$, and $Ca^{2+}$.

The iron oxide nanoparticles may generate a gigantic heat even in a biocompatible low AC magnetic field of $f_{appl} \cdot H_{appl}$ of $3.0 \times 10^9$ $Am^{-1}s^{-1}$ or less, and may have an intrinsic loss power (ILP) of 13.5 $nHm^2/Kg$ to 14.5 $nHm^2/Kg$ in an AC magnetic field of $f_{appl} \cdot H_{appl} < 1.8 \times 10^9$ $Am^{-1}s^{-1}$ ($f_{appl} < 120$ kHz, $H_{appl} < 15.12$ kA/m).

The iron oxide nanoparticles may be represented by $M_x$-$\gamma Fe_2O_3$ (M=Li, Na, K, Mg, and Ca), and x may satisfy $0.00 < x \leq 0.30$, preferably $0.10 \leq x \leq 0.25$, more preferably $0.10 \leq x \leq 0.20$.

The iron oxide nanoparticles may have an average particle diameter of about 7 nm to about 13 nm, without being limited thereto.

In accordance with another aspect of the present invention, a method of preparing iron oxide nanoparticles is applied to preparation of nanoparticles capable of being heated even in a biocompatible low AC magnetic field, and includes preparing iron oxide nanoparticles by mixing an $Fe^{3+}$ precursor, an $M^+$ or $M^{2+}$ (M=Li, Na, K, Mg, and Ca) precursor, a surfactant, and a solvent in an oxygen atmosphere caused by high temperature thermal decomposition (HTTD).

The $Fe^{3+}$ precursor and the $M^+$ or $M^{2+}$ (M=Li, Na, K, Mg, and Ca) precursor may include at least one selected from among metal nitrate, metal sulfate, metal acetylacetonate, metal fluoroacetoacetate, metal halide, metal perchlorate, metal alkyl oxide, metal sulfamate, metal stearate, and organic metal compounds, without being limited thereto. For example, for $Mg_x$-$\gamma Fe_2O_3$ nanoparticles, magnesium (Mg) acetate tetrahydrate and iron (Fe) acetylacetonate was used.

The solvent may include benzene solvents, hydrocarbon solvents, ether solvents, polymer solvents, ionic liquid solvents, halogen hydrocarbons, alcohols, sulfoxide solvents, water, and the like, preferably at least one of benzene, toluene, halobenzene, octane, nonane, decane, benzyl ether, phenyl ether, hydrocarbon ethers, polymer solvents, diethylene glycol (DEG), water, and ionic liquid solvents, without being limited thereto. For example, for $Mg_x$-$\gamma Fe_2O_3$ nanoparticles, benzyl ether was used.

In the method according to the present invention, the surfactant may be used to stabilize nanoparticles and may include at least one of organic acids ($C_n$COOH, $C_n$: hydrocarbon, $7 \leq n \leq 30$) including oleic acid, lauric acid, stearic acid, myristic acid, and hexadecanoic acid, without being limited thereto. For example, for $Mg_x$-$\gamma Fe_2O_3$ nanoparticles, oleic acid was used.

According to the present invention, the method of preparing iron oxide nanoparticles includes: (a) heating a mixed solution of an $Fe^{3+}$ precursor, an $M^+$ or $M^{2+}$ (M=Li, Na, K, Mg, and Ca) precursor, a surfactant, and a solvent to a temperature less than a boiling point of the solvent in a mixed atmosphere of oxygen and argon, followed by maintaining the mixed solution at the temperature for a certain period of time; (b) heating the mixed solution again to the boiling point of the solvent in a mixed atmosphere of oxygen and argon, followed by maintaining the mixed solution at the boiling point for a certain period of time; (c) removing a heating source and cooling the mixed solution to room temperature; and (d) performing precipitation and separation of nanoparticle powder by adding a polar solvent to the mixed solution and then performing centrifugation.

In the method of preparing iron oxide nanoparticles according to the present invention, a doping level can be adjusted by adjusting an amount of the $Fe^{3+}$ precursor or the $M^+$ or $M^{2+}$ (M=Li, Na, K, Mg, and Ca) precursor.

According to the present invention, the iron oxide nanoparticles can perform sufficient self-heating even in a biocompatible low AC magnetic field. Therefore, the iron oxide nanoparticles can be used for hyperthermia cancer treatment in a low AC magnetic field.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Hereinafter, exemplary embodiments of the present invention will be described in detail with reference to the accompanying drawings. It should be understood that the present invention is not limited to the following embodiments and may be embodied in different ways, and that the embodiments are provided for complete disclosure and thorough understanding of the invention by those skilled in the art.

According to the present invention, iron oxide nanoparticles are prepared by doping an Fe vacancy site of $\gamma$-$Fe_2O_3$ with an alkali metal ion or alkali earth metal ion, and generate gigantic heat even in a biocompatible low AC magnetic field. In hyperthermia, a biocompatible AC magnetic field generally has $f_{appl} \cdot H_{appl}$ of $5.0 \times 10^9$ $Am^{-1}s^{-1}$ or less, preferably $3.0 \times 10^9$ $Am^{-1}s^{-1}$ or less. The iron oxide nanoparticles according to the present invention can generate gigantic heat even in such a biocompatible low AC magnetic field.

As used herein, the expression "doped with . . . metal ion" means that a metal atom is doped and ion-bonded to surrounding atoms, and thus all of expressions "doped with . . . metal ion", "doped with . . . metal atom", and "doped with . . . metal" should be interpreted as having the same meaning.

The iron oxide nanoparticles according to the present invention generate heat in AC magnetic fields, and are preferably used in a biocompatible low AC magnetic field.

Hereinafter, as an example of the iron oxide nanoparticles according to the present invention, $Mg_x$-$\gamma Fe_2O_3$ will be described.

$Mg_x$-$\gamma Fe_2O_3$ is prepared by high-temperature thermal decomposition of an $Fe^{3+}$ precursor and an $Mg^{2+}$ precursor in an oxygen atmosphere, has a crystal structure in which an Fe vacancy site of $\gamma$-$Fe_2O_3$ is doped with $Mg^{2+}$, and generates gigantic heat even in a biocompatible low AC magnetic field.

Figure 1:
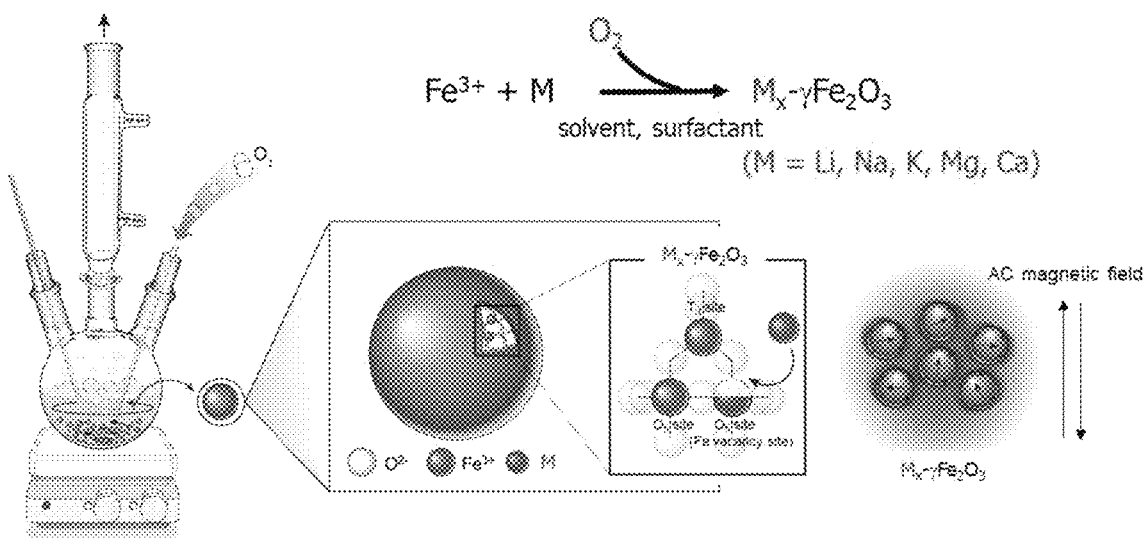
FIG. 1 is a diagram illustrating a method of preparing $M_x$-$\gamma Fe_2O_3$ (M=Li, Na, K, Mg, and Ca) nanoparticles according to an embodiment of the present invention.

A process of preparing $Mg_x$-$\gamma Fe_2O_3$ (x=0.13) will be described in more detail (see FIG. 1).

To prepare $Mg_{0.13}$-$\gamma Fe_2O_3$, 0.13 mmol of magnesium (Mg) acetate tetrahydrate, 2.0 mmol of iron (Fe) acetylacetonate, 1.2 mmol of oleic acid, and 20 mL of benzyl ether are mixed in a 50 mL round bottom flask and are magnetically stirred. The mixed solution is heated to 200° C. for 30 minutes (~8° C./min, first ramping up rate) in a mixed atmosphere of oxygen and argon (flow rate of ~100 mL/min) and is then maintained for 50 minutes (nucleation step). Next, the mixed solution is heated again to 296° C. (boiling point of benzyl ether) for 20 minutes (5° C./min, second ramping rate) and is then maintained for 60 minutes (growth step).

Next, a heating source is removed and the mixed solution is cooled to room temperature.

A polar solvent such as ethanol is added to the mixed solution, followed by centrifugation, thereby precipitating and separating black powder. Separated products (nanoparticles) are dispersed in a nonpolar solvent such as toluene.

To control the $Mg^{2+}$ doping concentration (x) of $Mg_x$-$\gamma Fe_2O_3$, the different amount of $Mg^{2+}$/$Fe^{3+}$ metal precursor are used under identical experimental conditions. For example, to synthesize the $Mg_{0.10}$-$\gamma Fe_2O_3$ nanoparticles, 0.10 mmol of Mg acetate tetrahydrate and 2.0 mmol of Fe acetylacetonate are used under the identical experimental conditions.

Figure 2:
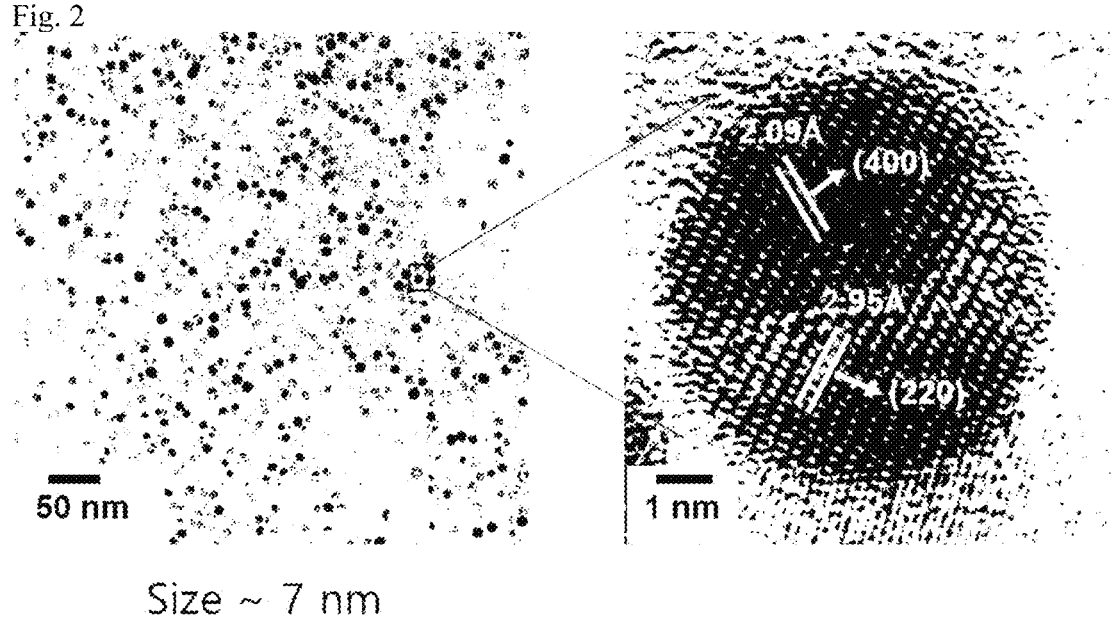
FIG. 2 shows transmission electron microscopy (TEM) images of $Mg_{0.13}$-$\gamma Fe_2O_3$ nanoparticles prepared according to an embodiment of the present invention.

FIG. 2 shows transmission electron microscope images of 7 nm $Mg_{0.13}$-$\gamma Fe_2O_3$ nanoparticles prepared through the above processes. Referring to the right-side image, it can be seen that a crystal growth orientation (400) is observed and the corresponding lattice distance is 2.09 Å, and that a crystal growth orientation (200) is observed and the corresponding lattice distance is 2.95 Å. These values are the same as those of a reference bulk material of $\gamma$-$Fe_2O_3$. Therefore, it can be proven that the crystal structure of nanoparticles prepared through the above processes has a typical spinel structure of $\gamma$-$Fe_2O_3$.

In a conventionally synthesized nanoparticles, $MgFe_2O_4$ nanoparticles ($Mg^{2+}$ doped $Fe_3O_4$ structure) are prepared.

To prepare $MgFe_2O_4$ nanoparticles, 1.0 mmol of $MgCl_2$ and 2.0 mmol of $Fe(acac)_3$ are placed in a 100 mL round bottom flask containing dibenzyl ether and a surfactant (oleic acid and oleylamine). 10.0 mmol of 1,2-hexadecandiol is used as a reductant.

The mixed solution is heated to 200° C. for 25 minutes in an argon atmosphere and maintained for 60 minutes (nucleation step).

Next, the mixed solution is heated again to 296° C. (boiling point of benzyl ether) for 30 minutes and maintained for 60 minutes. A heat source is removed and a reaction mixture is cooled to room temperature.

Ethanol is added to the reaction product, followed by centrifugation, thereby obtaining precipitated black powder. The obtained $MgFe_2O_4$ nanoparticles are dispersed in a nonpolar solvent such as toluene.

Upon preparation of existing nanoparticles, two chemical reagents, that is, oleic acid and oleylamine are used as size control factors, and oleylamine can be used as reducing agent. The crystal structure may be change $\gamma$-$Fe_2O_3$ into $Fe_3O_4$ during synthesis process thereof.

Oleylamine is mainly used in preparation of iron oxide nanoparticles. In order to investigate the role of surfactant, a control experiments were carried out with oleylamine instead of oleic acid. The nanoparticles synthesized with oleylamine showed a similar AC self-heating behavior to $MFe_2O_4$ (M=$Fe^{3+}$, $Co^{2+}$, $Ni^{2+}$, $Mg^{2+}$) nanoparticles due to the reduction of $Fe^{3+}$ into $Fe^{2+}$ that leads to the $Fe_3O_4$ lattice in the presence of oleylamine. This result confirms that $Mg^{2+}$ ion doped $Fe_3O_4$ lattice has no contribution to the AC heating properties.

$Mg_x$-$\gamma Fe_2O_3$, which corresponds to the iron oxide nanoparticles according to the present invention, is obtained by doping Fe vacancy sites of $\gamma$-$Fe_2O_3$ with $Mg^{2+}$.

Figure 3:
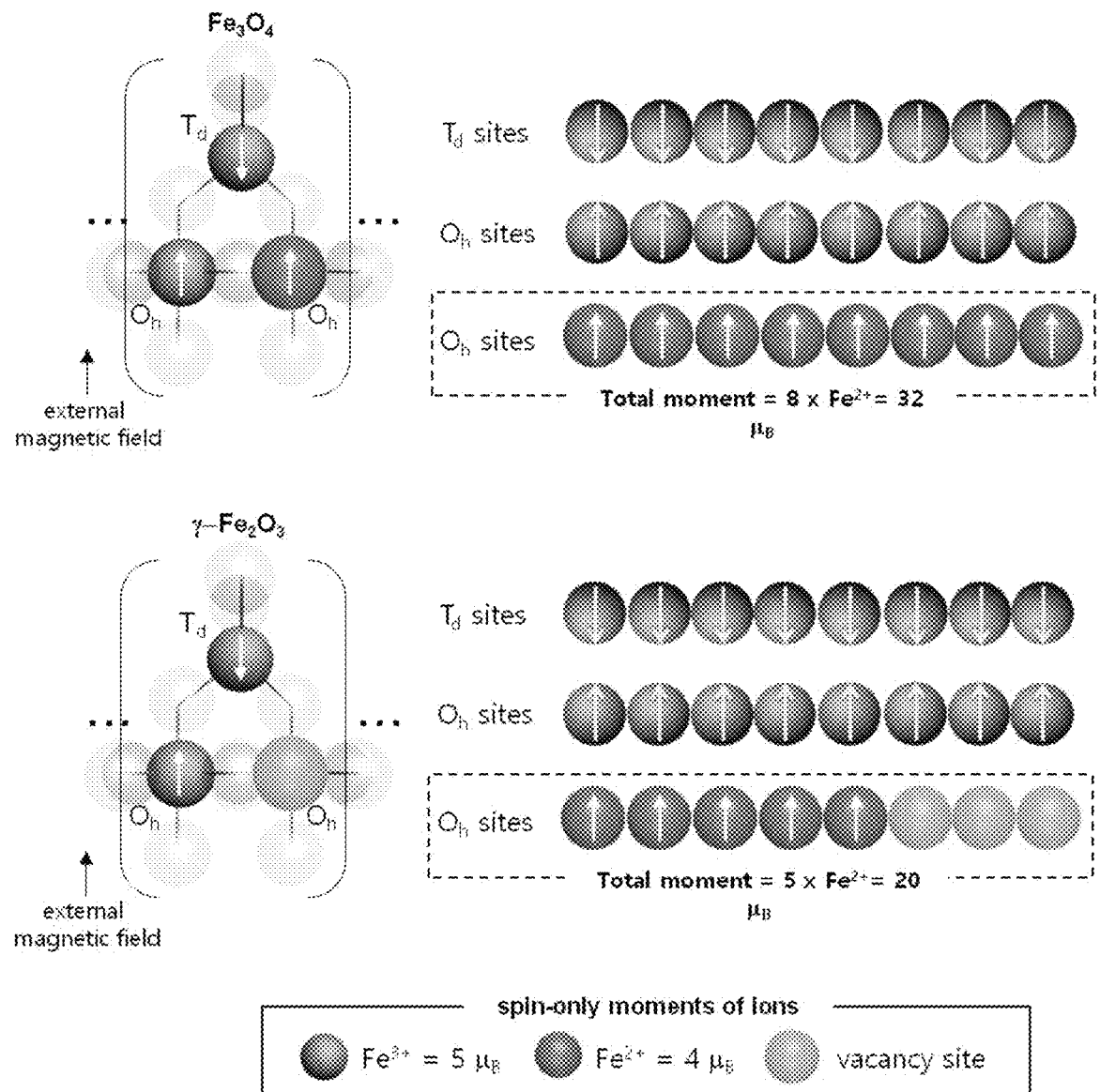
FIG. 3 are diagrams illustrating atomic structure models describing the spin configuration of $\gamma$-$Fe_2O_3$ (maghemite) and $Fe_3O_4$ (magnetite) magnetic nanoparticles according to an embodiment of the present invention.

Unlike $Fe_3O_4$, $\gamma$-$Fe_2O_3$ has spaces (vacancy sites), which occupy about 12% of the total volume thereof (see FIG. 3). Since $Fe_3O_4$ is gradually changed into $\gamma$-$Fe_2O_3$ upon preparation in an oxygen atmosphere, $Fe^{2+}$ ions present in $Fe_3O_4$ are oxidized to $Fe^{3+}$ ions, diffused out, and vacancy sites was formed in $\gamma$-$Fe_2O_3$. Since oxidation is required to prepare the iron oxide nanoparticles according to the present invention, preparation may be performed in an oxygen atmosphere, or an oxidant may be used. Actual preparation is preferably performed in a mixed atmosphere of oxygen and argon for stability of reaction.

Figure 4:
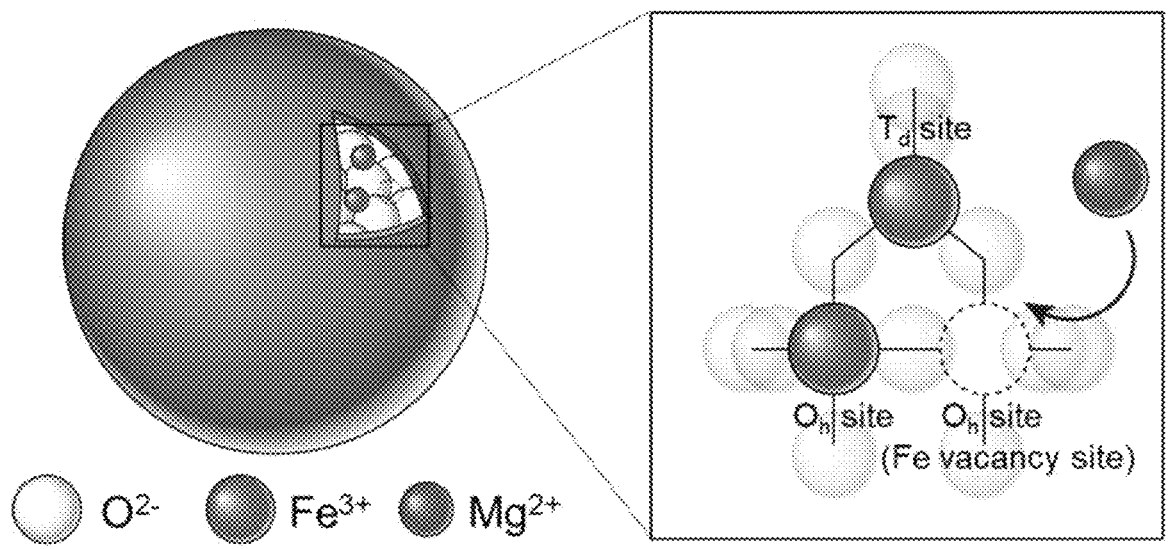
FIG. 4 are diagrams illustrating crystal structure of $Mg_{0.13}$-$\gamma Fe_2O_3$ (maghemite) magnetic nanoparticles according to an embodiment of the present invention. An enlarged image indicates that face-centered cubic lattices of oxygen (white sphere). The $Fe^{3+}$ (blue sphere) spins at $T_d$ sites aligns in antiparallel with $Fe^{3+}$ spins at $O_h$ sites under external magnetic field. The $Mg^{2+}$ (red sphere) ions predominantly occupy the Fe vacancy sites existing in the $O_h$ sites of $\gamma$-$Fe_2O_3$.

When such vacancy sites of $\gamma$-$Fe_2O_3$ is doped with an alkali metal or alkali earth metal, the doped $\gamma$-$Fe_2O_3$ demonstrate change in DC/AC magnetic softness and magnetic properties, specifically magnetic susceptibility, and thus responds to a low AC magnetic field, thereby generating heat (see FIG. 4).

On the other hand, unlike the above case, in the case of a transition metal (Zn, Fe, Mn, Co, Ni, and the like), since it is energetically favorable in terms of thermodynamics that the transition metal is predominantly substituted with $Fe^{3+}$ ions at an octahedral site ($O_h$) and a tetrahedral site ($T_h$), not in vacancy site, doped γ-Fe$_2$O$_3$ exhibits reduced net magnetic properties and respond negligibly to a low AC magnetic field (see FIGS. 3 and 4).

The iron oxide nanoparticles according to the present invention are nanoparticles in which Fe vacancy sites of γ-Fe$_2$O$_3$ are doped with an alkali metal or alkali earth metal. According to the present invention, a doping metal includes any alkali metal or alkali earth metal without limitation. Preferably, the alkali metal is lithium (Li), sodium (Na), or potassium (K), and the alkali earth metal is magnesium (Mg) or calcium (Ca).

In addition, the iron oxide nanoparticles according to the present invention are doped with at least one alkali metal or alkali earth metal, preferably at least one metal ion selected from the group consisting of Li$^+$, Na$^+$, K$^+$, Mg$^{2+}$, and Ca$^{2+}$.

The iron oxide nanoparticles according to the present invention may emit gigantic heat even in a biocompatible low AC magnetic field of $f_{appl} \cdot H_{appl}$ of $3.0 \times 10^9$ Am$^{-1}$s$^{-1}$ or less, and have an intrinsic loss power (ILP) of 13.5 nHm$^2$/Kg to 14.5 nHm$^2$/Kg in an AC magnetic field of $f_{appl} \cdot H_{appl} < 1.8 \times 10^9$ Am$^{-1}$s$^{-1}$ ($f_{appl} < 120$ KHz, $H_{appl} < 15.12$ KA/m).

Further, the iron oxide nanoparticles according to the present invention may be represented by M$_x$-γFe$_2$O$_3$ (M=Li, Na, K, Mg, and Ca), and x may vary with a doping concentration of a metal. x satisfies 0.00<x≤0.30, preferably 0.10≤x≤0.25, more preferably 0.10≤x≤0.20.

The iron oxide nanoparticles according to the present invention have an average particle diameter of about 7 nm to about 13 nm, without being limited thereto, and may have various nanometer scale sizes.

Figure 5:
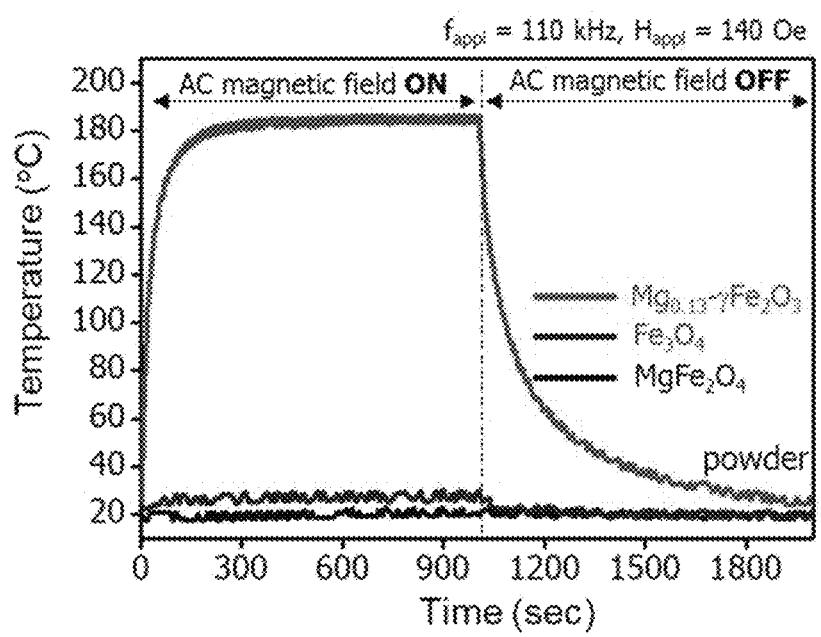
FIG. 5 is a graph depicting AC magnetically-induced heating characteristics of $Mg_{0.13}$-$\gamma Fe_2O_3$, $MgFe_2O_4$, and $Fe_3O_4$ measured at a $f_{appl}$=110 KHz and $H_{appl}$=±140 Oe according to an embodiment of the present invention.

FIG. 5 is a graph depicting AC magnetically-induced heating characteristics of Mg$_{0.13}$-γFe$_2$O$_3$, MgFe$_2$O$_4$, and Fe$_3$O$_4$ measured at a low AC magnetic field ($f_{appl}$=110 kHz, $H_{appl}$=±140 Oe) according to an embodiment of the present invention. As shown in FIG. 5, Mg$_{0.13}$-γFe$_2$O$_3$ nanoparticles exhibits an exceptionally high T$_{ac,max}$ of 180° C. While, conventionally prepared MgFe$_2$O$_4$ (Mg$^{2+}$ ion doped Fe$_3$O$_4$) nanoparticles exhibits a low T$_{ac,max}$ of 22° C. under same AC magnetic field. According to an conventional method have almost no effect of heat emission at a low AC magnetic field.

Figure 6:
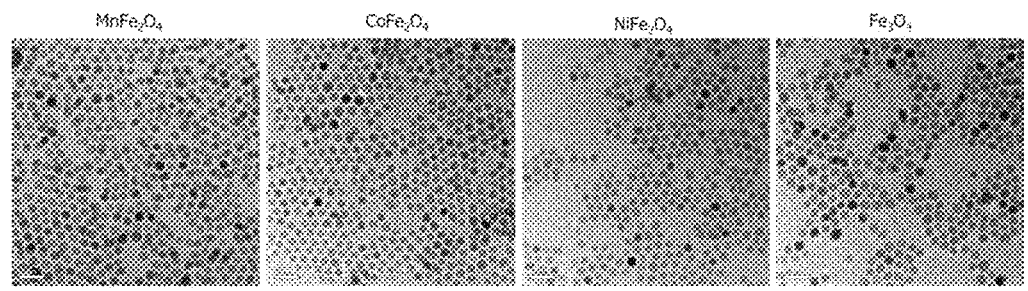
FIG. 6 shows transmission electron microscopy (TEM) images of $MFe_2O_4$ (M=Mn, Co, Ni, Fe) nanoparticles prepared by a conventional method and a graph depicting AC magnetically-induced heating characteristics thereof in a low AC magnetic field.
Figure 6:
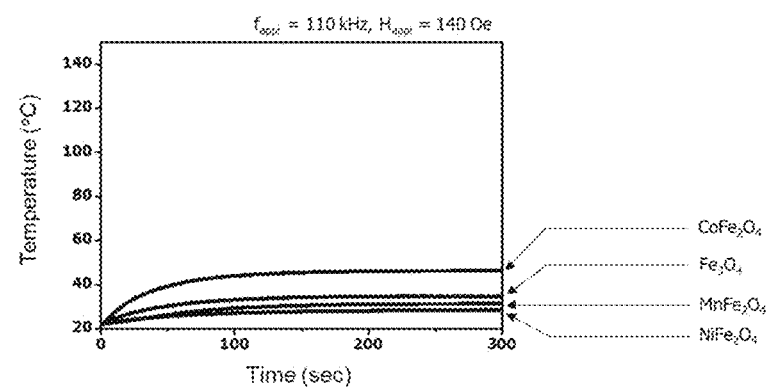

FIG. 6 shows a graph depicting transmission electron microscopy images and AC magnetically-induced heating characteristics of MFe$_2$O$_4$ (M=Co$^{2+}$, Fe$^{2+}$, Mn$^{2+}$, and Ni$^{2+}$) nanoparticles, which are prepared by a conventional method under the same AC magnetic conditions ($f_{appl}$=110 kHz, $H_{appl}$=±140 Oe). It can be seen that conventionally synthesized nanoparticles (CoFe$_2$O$_4$, Fe$_3$O$_4$, MnFe$_2$O$_4$, and NiFe$_2$O$_4$) have almost no effect of heat emission. CoFe$_2$O$_4$, Fe$_3$O$_4$, MnFe$_2$O$_4$, and NiFe$_2$O$_4$ have a structure in which Co$^{2+}$, Fe$^{2+}$, Mn$^{2+}$, and Ni$^{2+}$ ions are doped into Fe$_3$O$_4$ instead of γ-Fe$_2$O$_3$, respectively.

Figure 7:
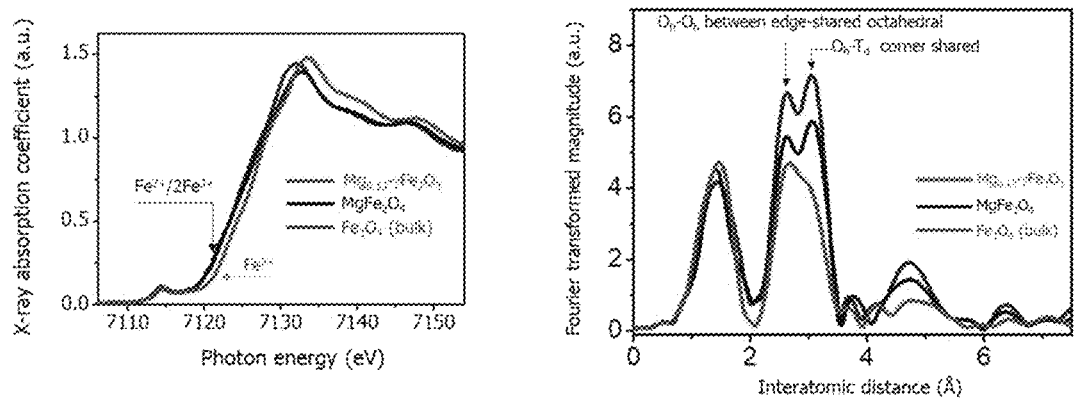
FIG. 7 shows graphs depicting X-ray absorption spectroscopy (left: X-ray absorption near edge structure, right: extended X-ray absorption fine structure) measurement results of $Mg_{0.13}$-$\gamma Fe_2O_3$, $MgFe_2O_4$, and bulk $Fe_3O_4$.

FIG. 7 shows X-ray absorption near edge structure (XANES) and extended X-ray absorption fine structure (EXAFS) measurement results of Mg$_{0.13}$-γFe$_2$O$_3$ nanoparticles. For comparison, conventional MgFe$_2$O$_4$ nanoparticles and bulk Fe$_3$O$_4$ was prepared. The Fe K-edge XANES spectra (left-side graph in FIG. 7) showed that Mg$_{0.13}$-γFe$_2$O$_3$, and MgFe$_2$O$_4$ nanoparticles have average iron oxidation states of +3, and +2.75, respectively. Comparing to bulk Fe$_3$O$_4$, MgFe$_2$O$_4$ nanoparticles have a typical local Fe coordination of Fe$_3$O$_4$ while, according to the EXAFS analyzed results (right-side graph in FIG. 7), it was confirmed that Mg$_{0.13}$-γFe$_2$O$_3$ nanoparticles has a typical γ-Fe$_2$O$_3$ (maghemite). In contrast, conventionally synthesized MgFe$_2$O$_4$ nanoparticles are obtained by doping Mg$^{2+}$ into a magnetite (Fe$_3$O$_4$) structure, and that the Mg$_{0.13}$-γFe$_2$O$_3$ nanoparticles according to the present invention are obtained by doping Mg$^{2+}$ into a maghemite (γ-Fe$_2$O$_3$) structure.

Figure 8:
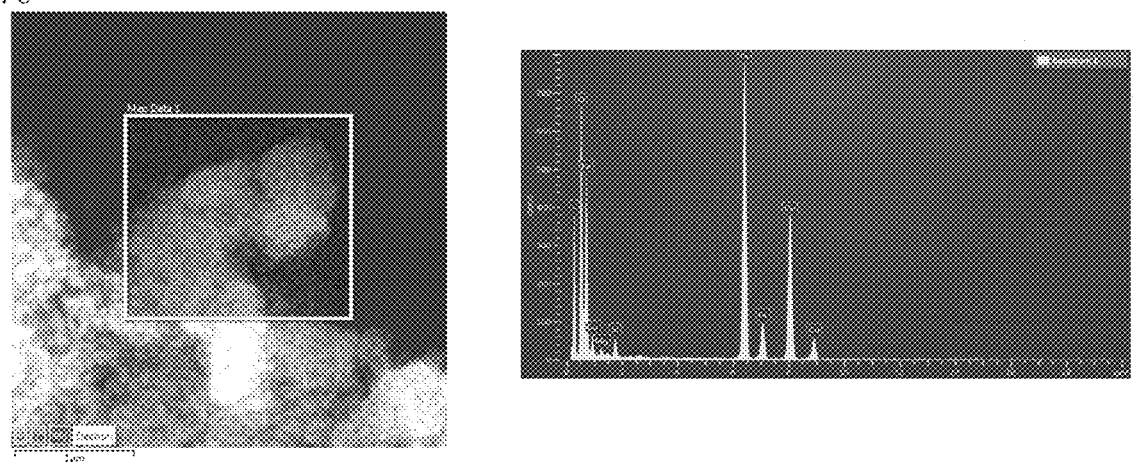
FIG. 8 is a diagram showing composition determination of $Mg_{0.13}$-$\gamma Fe_2O_3$ by energy dispersive X-ray spectroscopy (EDS).

FIG. 8 shows composition determination results of Mg$_{0.13}$-γFe$_2$O$_3$ nanoparticles using an energy dispersive X-ray spectroscopy (EDS), and it can be seen that Mg$^{2+}$ ions is well presented in γ-Fe$_2$O$_3$ nanoparticles.

Figure 9:
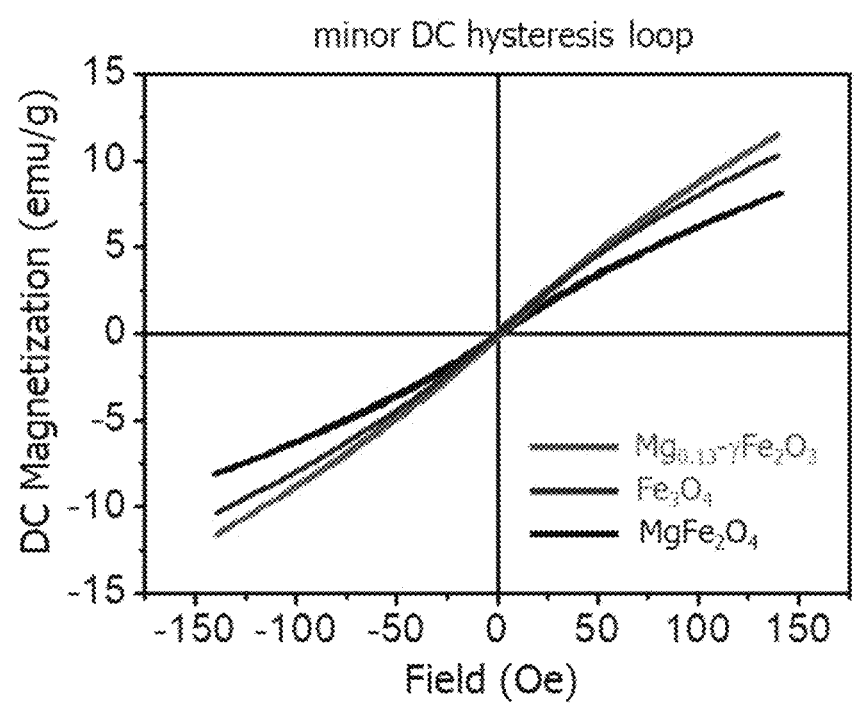
FIG. 9 shows DC minor hysteresis loops measured at a sweeping field of $H_{appl}$=±140 Oe (=11.14 $KAm^{-1}$) of $Mg_{0.13}$-$\gamma Fe_2O_3$, $MgFe_2O_4$, and $Fe_3O_4$.
Figure 10:
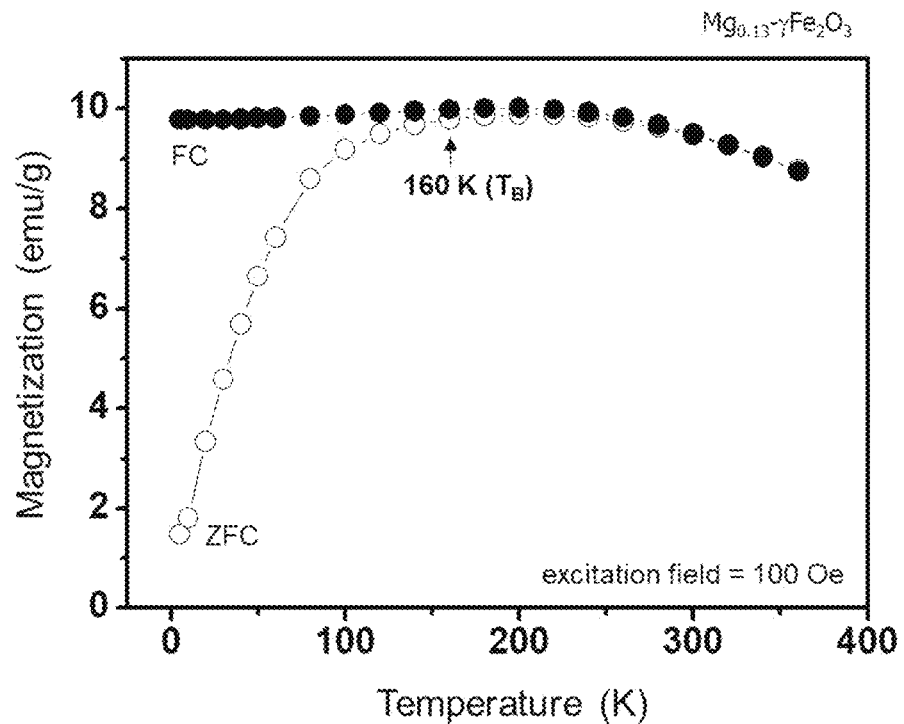
FIG. 10 is a graph depicting a temperature dependent magnetization of $Mg_{0.13}$-$\gamma Fe_2O_3$ nanoparticles measured at an excitation magnetic field of 100 Oe.

FIG. 9 shows DC minor hysteresis loops and FIG. 10 shows the temperature dependent magnetization of Mg$_{0.13}$-γFe$_2$O$_3$ nanoparticles. Referring to FIGS. 9 and 10, it can be proven that Mg$_{0.13}$-γFe$_2$O$_3$ according to the present invention exhibits superparamagnetism.

Figure 11:
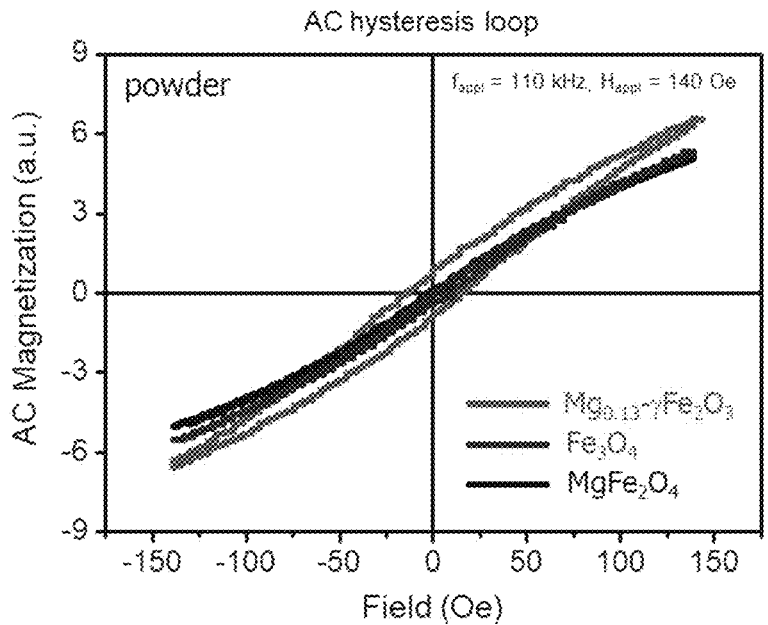
FIG. 11 shows AC hysteresis loops measured at a $f_{appl}$=110 KHz and $H_{appl}$=±140 Oe of $Mg_{0.13}$-$\gamma Fe_2O_3$, $MgFe_2O_4$, and $Fe_3O_4$.

FIG. 11 shows the area of AC hysteresis loops measured at a $f_{appl}$=110 KHz and $H_{appl}$=±140 Oe of Mg$_{0.13}$-γFe$_2$O$_3$, MgFe$_2$O$_4$, and Fe$_3$O$_4$. Mg$_{0.13}$-γFe$_2$O$_3$ nanoparticles had the much larger area than those of MgFe$_2$O$_4$ and Fe$_3$O$_4$. The larger AC hysteresis loss area of Mg$_{0.13}$-γFe$_2$O$_3$ indicates that it has a higher AC magnetic softness (or faster AC magnetic response). Thus, it can be proven that the Mg$_{0.13}$-γFe$_2$O$_3$ nanoparticles according to the present invention exhibit gigantic (or exceptionally high) heat emission.

Figure 12:
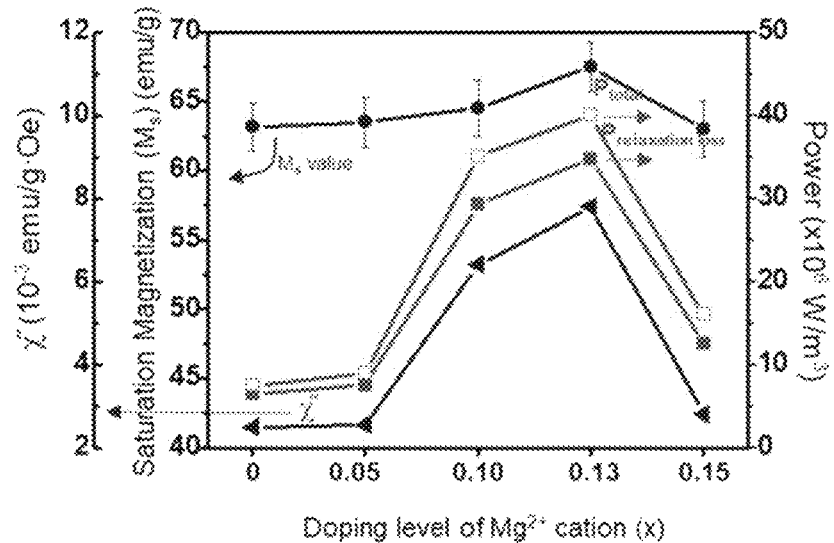
FIG. 12 shows graphs depicting the dependence of $M_s$, $P_{total}$, $P_{relaxation\ loss}$, and $\chi''$ on the $Mg^{2+}$ cation doping concentration (level) (x) of $Mg_x$-$\gamma Fe_2O_3$ according to an embodiment of the present invention.

FIG. 12 shows graphs depicting the dependence of M$_s$, P$_{total}$, P$_{relaxation\ loss}$, and χ''$_m$ on the Mg$^{2+}$ cation doping concentration (x) of Mg$_x$-γFe$_2$O$_3$ nanoparticles. The χ''$_m$ (and P$_{relaxation-loss}$) was dramatically increased from 2.51× 10$^{-3}$ emu·g$^{-1}$Oe$^{-1}$ (6.84×10$^6$ W/m$^3$) to 7.574×10$^{-3}$ emu·g$^{-1}$Oe$^{-1}$ (3.42×10$^6$ W/m$^7$) by increasing the doping concentration of Mg$^{2+}$ ion up to 0.13 and P$_{total}$ was correspondingly increased from 7.82×10$^6$ W/m$^3$ to 4×10$^7$ W/m$^3$. However, the further increase the doping concentration of Mg$^{2+}$ ion up to 0.15 led to severe reduction of χ''$_m$ (P$_{Néel-relaxation-loss}$), M$_s$, and P$_{total}$. The increase of Mg$^{2+}$ ion doping concentration from 0 to 0.13 during the synthesis leads to the acceleration of occupation of Fe vacancy sites by Mg$^{2+}$ ions in γ-Fe$_2$O$_3$ lattice so that results in the increase of Mg$^{2+}$ doping concentration that would be mainly responsible for the significant enhancement of M$_s$ (χ''$_m$). On the contrary, the sudden decrease of χ''$_m$, P$_{total}$, and M$_s$ at x=0.15 can be supposed to be due to the reduction of Mg$^{2+}$ doping concentration in Fe vacancy sites in γ-Fe$_2$O$_3$ resulted from the substitution of Fe$^{3+}$ in the O$_h$ site by Mg$^{2+}$ cations. Referring to FIG. 12, it can be seen that the Mg$_x$-γFe$_2$O$_3$ nanoparticles emit a large amount of heat when x satisfies 0.05≤x≤0.15. The Mg$_x$-γFe$_2$O$_3$ nanoparticles theoretically emit the largest amount of heat in the case of x=0.13, and it can be seen that this coincides with the experimental results.

Figure 13:
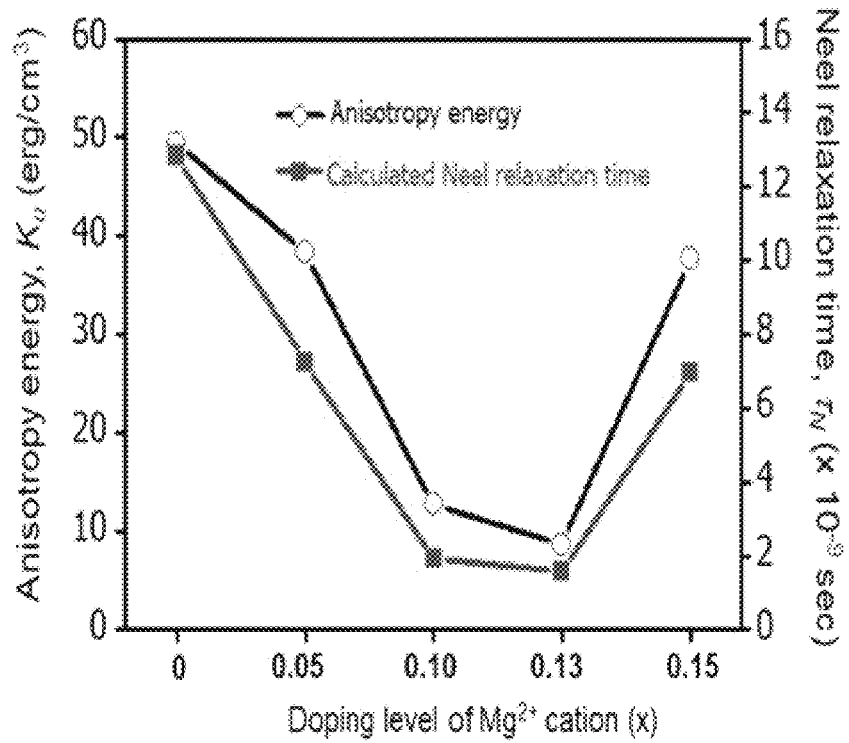
FIG. 13 shows graphs depicting the dependence of anisotropy energy and calculated Neel relaxation time on $Mg^{2+}$ cation doping concentration (x) in $Mg_x$-$\gamma Fe_2O_3$ according to an embodiment of the present invention.

FIG. 13 shows graphs depicting the dependence of anisotropy energy and calculated Neel relaxation time on Mg$^{2+}$ cation doping concentration (x) in Mg$_x$-γFe$_2$O$_3$ nanoparticles. The physical reason for the obvious increase of χ''$_m$ (P$_{Néel-relaxation-loss}$) depending on the Mg$^{2+}$ cation doping concentration is thought to be primarily due to the enhanced τ$_N$ (faster τ$_N$) that is resulted from the change of AC magnetic softness or magnetic anisotropy caused by the modification of Mg$^{2+}$ doping concentration in Fe vacancy sites of γ-Fe$_2$O$_3$.

Figure 14:
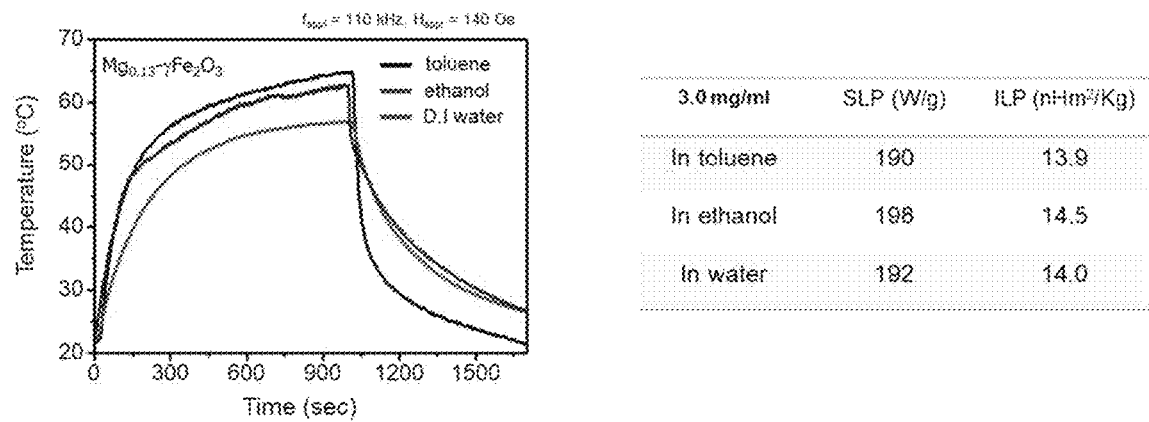
FIG. 14 shows characteristics of AC magnetically-induced heating temperature rise of $Mg_{0.13}$-$\gamma Fe_2O_3$ nanofluids dispersed in toluene, ethanol, and D.I water measured at a $f_{appl}$=110 KHz and $H_{appl}$=±140 Oe with a concentration of 3 mg/mL according to an embodiment of the present invention are moved to an aqueous solution layer.

FIG. 14 shows characteristics of AC magnetically-induced heating temperature rise of Mg$_{0.13}$-γFe$_2$O$_3$ nanofluids dispersed in toluene, ethanol, and D.I water measured at a $f_{appl}$=110 KHz and $H_{appl}$=±140 Oe with a concentration of 3 mg/mL Referring to FIG. 14, it can be confirmed that the Mg$_{0.13}$-γFe$_2$O$_3$ iron oxide nanoparticles according to the present invention have an intrinsic loss power (ILP) value of about 13.9 nHm$^2$ kg$^{-1}$ (in toluene), a 14.5 nHm$^2$ kg$^{-1}$ (in ethanol), and a 14.0 nHm$^2$ kg$^{-1}$ (in water), respectively.

Figure 15:
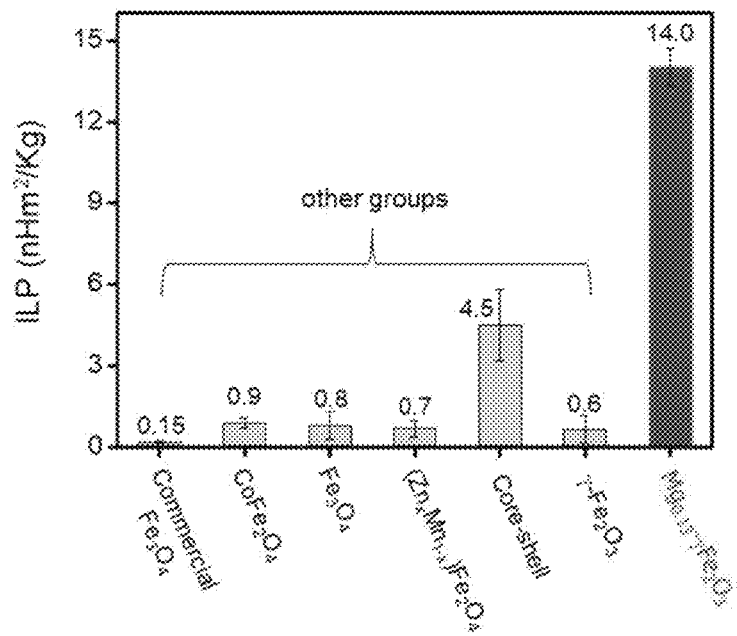
FIG. 15 is a graph for comparison of ILP values between previously reported superparamagnetic nanoparticles and $Mg_{0.13}$-$\gamma Fe_2O_3$ superparamagnetic nanoparticles according to an embodiment of the present invention and existing representative materials known in the art.

FIG. 15 is a graph for comparison of ILP values between iron oxide nanoparticles according to the present invention and previously reported superparamagnetic nanoparticles known in the art. Referring to FIG. 15, it can be confirmed that the iron oxide nanoparticles according to the present invention have an ILP value that is about 100 times higher than that of commercial $Fe_3O_4$ (Feridex) nanoparticles.

Figure 16:
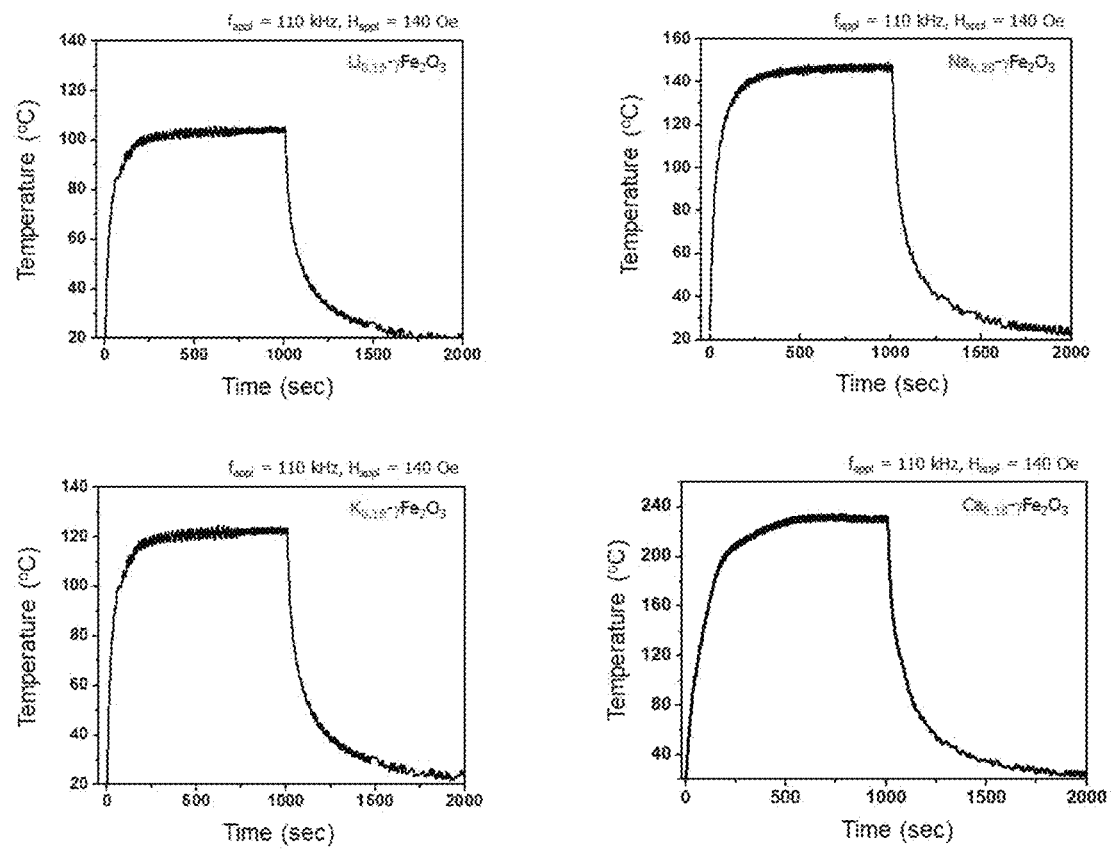
FIG. 16 shows graphs depicting characteristics of AC magnetically-induced heating temperature rise of $Li_{0.15}$-$\gamma Fe_2O_3$, $Na_{0.20}$-$\gamma Fe_2O_3$, $K_{0.18}$-$\gamma Fe_2O_3$, and $Ca_{0.18}$-$\gamma Fe_2O_3$ nanoparticles according to an embodiment of the present invention with $Li^+$, $Na^+$, $K^+$, and $Ca^{2+}$, respectively, in a low AC magnetic field.

FIG. 16 shows graphs depicting characteristics of AC magnetically-induced heating temperature rise of $Li_{0.15}$-$\gamma Fe_2O_3$, $Na_{0.20}$-$\gamma Fe_2O_3$, $K_{0.18}$-$\gamma Fe_2O_3$, and $Ca_{0.18}$-$\gamma Fe_2O_3$ nanoparticles, respectively, in a low AC magnetic field ($f_{appl}$=110 kHz, $H_{appl}$=±140 Oe). It can be confirmed that all the nanoparticles ($Li_{0.15}$-$\gamma Fe_2O_3$, $Na_{0.20}$-$\gamma Fe_2O_3$, $K_{0.18}$-$\gamma Fe_2O_3$, and $Ca_{0.18}$-$\gamma Fe_2O_3$) exhibited an exceptionally high $T_{AC,max}$ above 100° C. Therefore, it can be seen that all of the $M_x$-$\gamma Fe_2O_3$ (M=Li, Mg, K, Na, and Ca) nanoparticles according to the present invention, which are obtained by doping $\gamma$-$Fe_2O_3$ with Mg or by doping $\gamma Fe_2O_3$ with a different alkali metal or alkali earth metal from Mg, exhibit high AC self-heating in a low AC magnetic field.

Figure 17:
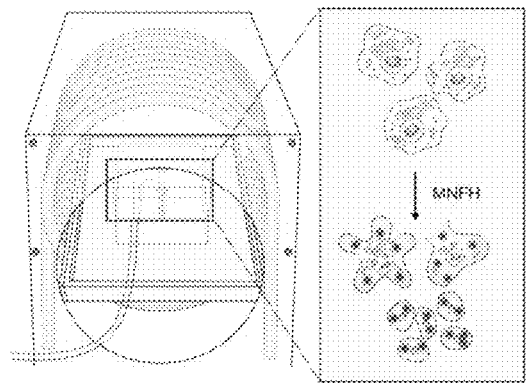
FIGS. 17 to 19 show results obtained by an in-vitro hyperthermia test using $Mg_{0.13}$-$\gamma Fe_2O_3$ magnetic nanoparticles according to an embodiment of the present invention.
Figure 17:
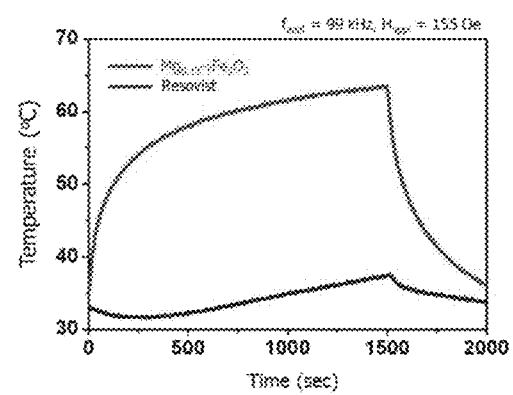

FIG. 17 show results obtained by an in-vitro hyperthermia test using U87MG cells after treating $Mg_{0.13}$-$\gamma Fe_2O_3$ magnetic nanoparticles and Resovist.

The U87MG cells were incubated with 700 μg/mL of $Mg_{0.13}$-$\gamma Fe_2O_3$ nanofluids and Resovist, as a control group, for cellular uptake. The cells were placed in the center of an AC magnetic coil, and a magnetic field of $f_{appl}$=99 kHz and $H_{appl}$=±155 Oe ($H_{appl} \cdot f_{appl}$=1.22×10$^9$ Am$^{-1}$s$^{-1}$) was applied to the cells for 1500 seconds. Referring to the right-side graph of FIG. 17, it can be confirmed that the cells treated with $Mg_{0.13}$-$\gamma Fe_2O_3$ nanofluids showed the much higher $T_{AC,max}$ (63.5° C.) than Resovist (37.5° C.).

Figure 18:
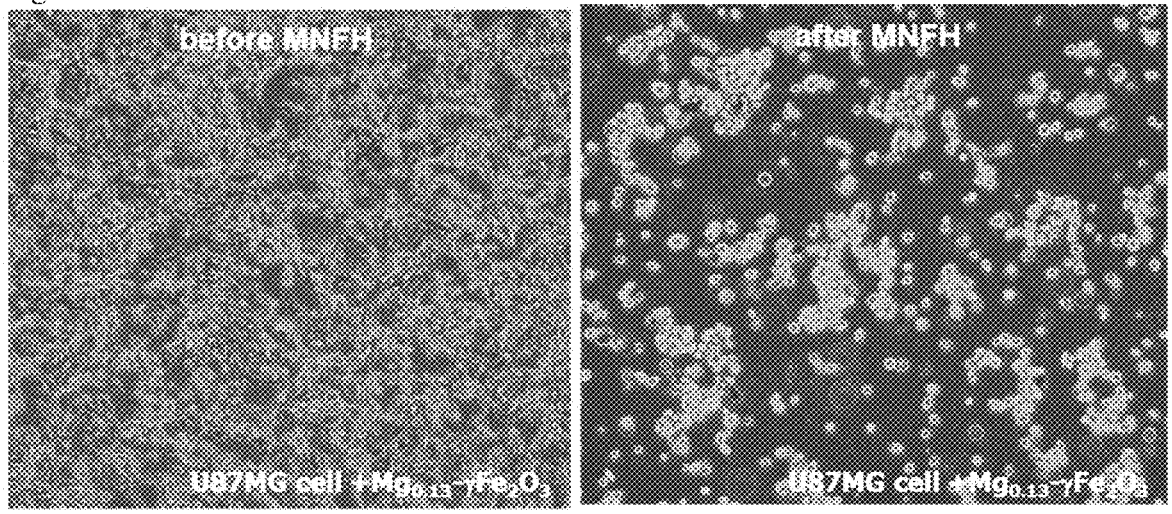

Referring to FIG. 18 showing the optical microscope images of U87MG cells before and after magnetic nanofluid hyperthermia with $Mg_{0.13}$-$\gamma Fe_2O_3$ nanofluids, it can be confirmed that the cell necrosis of U87MG resulted from severe deformation and shrinkage of the cell morphology caused by the applied thermal energy was clearly observed after magnetic nanofluid hyperthermia, all cancer cells were killed by heat. In more detail, it was confirmed that 75% of the cancer cells were killed at 48° C. and all of the cancer cells were completely necrotized at 63.5° C. Thus, bioavailability of the nanoparticles according to the present invention was proven.

Figure 19:
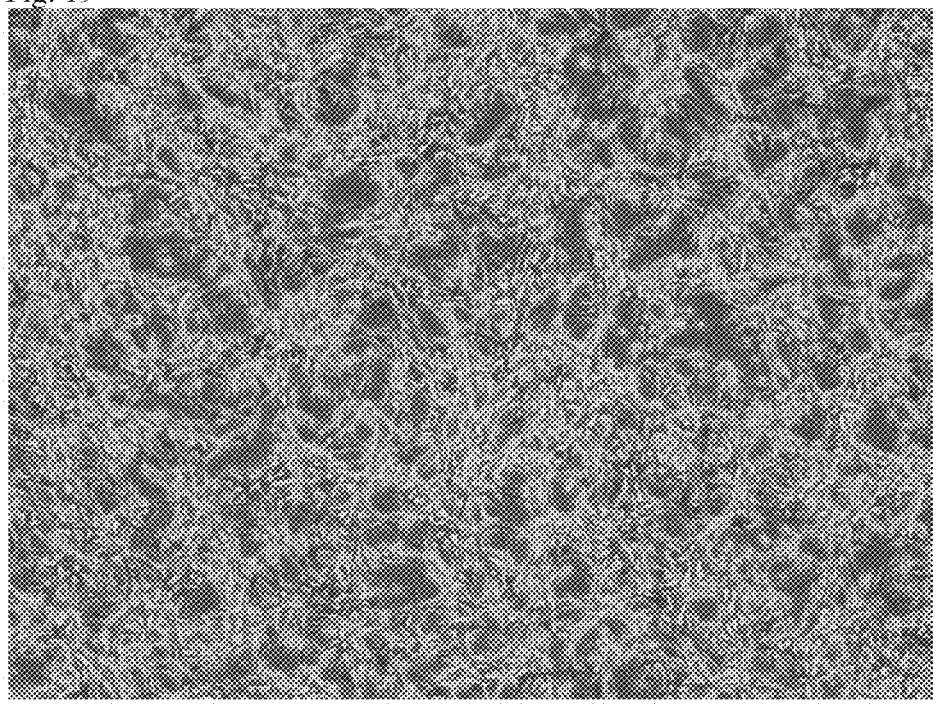

On the other hand, FIG. 19 is an image showing the optical microscope image of U87MG cells after magnetic nanofluid hyperthermia with Resovist (control group), and cells suffering from deformation or shrinkage were not observed. Thus, it can be seen that cell viability was strongly dependent on AC heating temperature.

Figure 20:
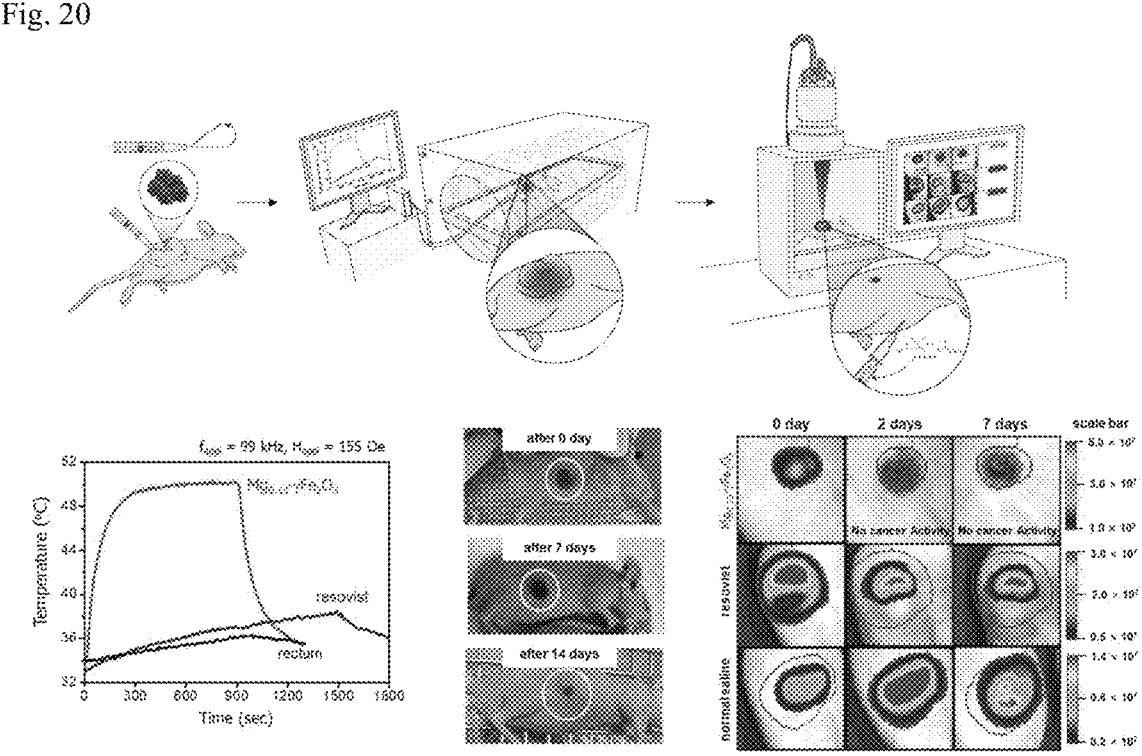
FIG. 20 shows results obtained by an in-vivo hyperthermia test using $Mg_{0.13}$-$\gamma Fe_2O_3$ magnetic nanoparticles according to an embodiment of the present invention.

FIG. 20 shows results obtained by an in-vivo hyperthermia test using $Mg_{0.13}$-$\gamma Fe_2O_3$ magnetic nanoparticles.

Hep3B cells transfected with luciferase (for bioluminescence imaging, BLI) grew subcutaneously in mice (cancer-xenograft model)

A 100 μL of $Mg_{0.13}$-$\gamma Fe_2O_3$ nanofluids (100 μL, 11.5 μg/μL) was intratumorally injected into cancer cells of the mice (~1000 mm$^3$) through soft tissue using a bent needle and optical thermometers were mounted in the cancer cells and rectum area to monitor the temperature.

For comparison, Resovist (100 μL, 11.5 μg/μL) and normal saline (100 μL, 11.5 μg/μL) were also intratumorally injected into the mice, respectively.

The mice were placed in the center of an AC magnetic coil and exposed to an AC magnetic field ($f_{appl}$=99 kHz, $H_{appl}$=±155 Oe, $H_{appl} \cdot f_{appl}$=1.22×10$^9$ Am$^{-1}$s$^{-1}$) for 900 seconds.

The temperature of the rectum and Hep3B injected with Resovist were slightly increased from 34° C. to 36.37° C. and 37.14° C., respectively. However, the temperature of the Hep3B cells injected with the $Mg_{0.13}$-$\gamma Fe_2O_3$ nanofluids was rapidly increased up to 50.2° C. (thermoablation temperature).

The activity of the Hep3B was analyzed by employing a bioluminescence imaging (BLI) technique. The Hep3B treated with $Mg_{0.13}$-$\gamma Fe_2O_3$ nanofluids did not exhibit any BL-intensity from day 2 after magnetic nanofluid hyperthermia, while the control groups still exhibited strong BL-intensity after magnetic nanofluid hyperthermia. No BL-intensity means that the cancer cells was completely necrotized by magnetic nanofluid hyperthermia.

Figure 21:
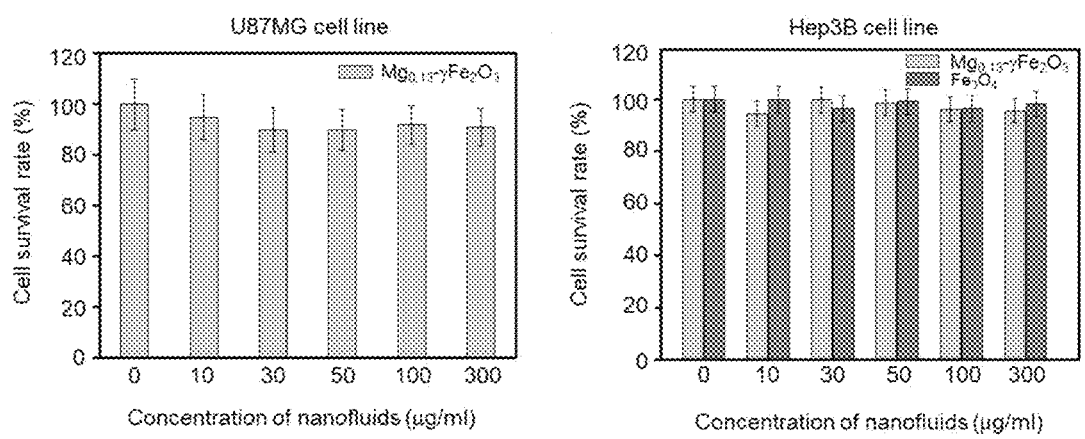
FIG. 21 shows graphs depicting results obtained by a toxicity test of $Mg_{0.13}$-$\gamma Fe_2O_3$ magnetic nanoparticles according to an embodiment of the present invention on U87MG cells and Hep3B cells.

FIG. 21 shows graphs depicting results obtained by a toxicity test of $Mg_{0.13}$-$\gamma Fe_2O_3$ magnetic nanoparticles according to the present invention on U87MG cells and Hep3B cells. From the this result, it was confirmed that $Mg_{0.13}$-$\gamma Fe_2O_3$ nanoparticles showed a high biocompatibility (non-toxicity) even at a higher concentration (300 μg/mL).

Figure 22:
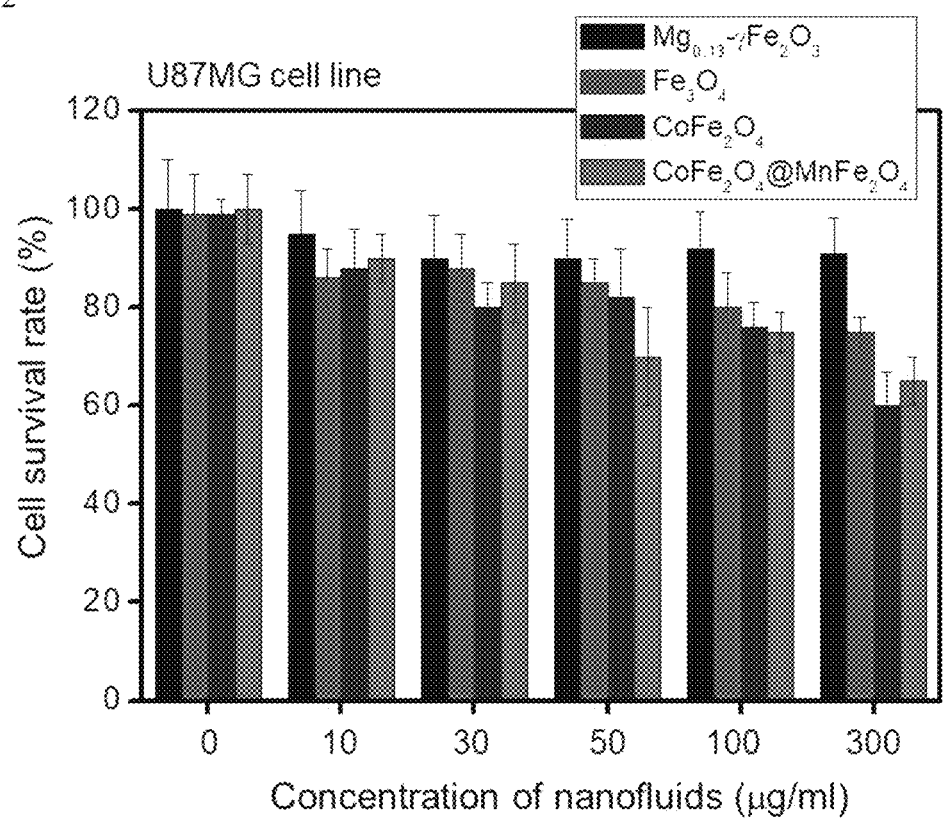
FIG. 22 shows graphs depicting cell survival rate of $Mg_{0.13}$-$\gamma Fe_2O_3$ nanoparticles and reported superparamagnetic nanoparticles determined using U87MG cell lines.

FIG. 22 shows graphs depicting cell survival rate of $Mg_{0.13}$-$\gamma Fe_2O_3$ nanoparticles and reported superparamagnetic nanoparticles determined using U87MG cell lines. $Mg_{0.13}$-$\gamma Fe_2O_3$ nanoparticles had a higher biocompatibility (non-toxicity) with U87Mg cell lines compared to all other reported superparamagnetic nanoparticles even at a higher concentration (300 μg/mL). The reported nanoparticles ($Fe_3O_4$, $CoFe_2O_4$, $CoFe_2O_4@MnFe_2O_4$) have a $Fe_3O_4$ crystal structure. In the case of $Fe_3O_4$, the Fenton reaction is likely to occur and produce a toxic effect to the cells during cellular internalization due to the $Fe^{2+}$ ions in $Fe_3O_4$ lattice. However, $Mg_{0.13}$-$\gamma Fe_2O_3$ nanoparticles, which is fully oxidized forms from $Fe_3O_4$, has only $Fe^{3+}$ ions in $\gamma$-$Fe_2O_3$ lattice crystal. Hence the possibility to occur Fenton reaction is readily expected to be an extremely low during cellular internalization.

As described above, it was proven through both of the in-vitro and in-vivo tests that cancer cells could be completely killed using magnetic nanoparticles according to the present invention. Therefore, the iron oxide nanoparticles according to the present invention can be clinically used.

Heretofore, the present invention has been described with reference to some embodiments in conjunction with the accompanying drawings. Although specific terms are used herein, it should be understood that the terms are only for the purpose of describing the embodiments of the present invention and are not intended to limit the present invention. In addition, it should be understood that various modifications, changes, alterations, and equivalent embodiments can be made by those skilled in the art without departing from the spirit and scope of the present invention. Therefore, the scope of the present invention should be defined only by the accompanying claims and equivalents thereof.

What is claimed is:

1. Iron oxide nanoparticles in which $\gamma$-$Fe_2O_3$ is doped with an alkali metal or alkali earth metal, wherein:
    an Fe vacancy site of $\gamma$-$Fe_2O_3$ is doped with the alkali metal or alkali earth metal;
    the iron oxide nanoparticles generate heat in a biocompatible AC magnetic field of $f_{appl} \cdot H_{appl}$ of 3.0×10$^9$ Am$^{-1}$s$^{-1}$ or less;
    the iron oxide nanoparticles are represented by $M_x$-$\gamma Fe_{2-x}O_3$, where M is selected from the group consisting of Li, Na, K, Mg, and Ca, and x satisfies 0.05≤x≤0.15; and
    the iron oxide nanoparticles are superparamagnetic.

2. The iron oxide nanoparticles according to claim 1, wherein M is an alkali metal selected from the group consisting of lithium (Li), sodium (Na), and potassium (K).

3. The iron oxide nanoparticles according to claim 1, wherein M is an alkali earth metal selected from the group consisting of magnesium (Mg) and calcium (Ca).

4. The iron oxide nanoparticles according to claim 1, wherein the iron oxide nanoparticles generate heat in a biocompatible AC magnetic field of $f_{appl} \cdot H_{appl}$ of $1.8 \times 10^9$ $Am^{-1}s^{-1}$ ($f_{appl}$<120 kHz, $H_{appl}$<15.12 kA/m) or less.

5. The iron oxide nanoparticles according to claim 1, wherein the iron oxide nanoparticles have an intrinsic loss power (ILP) of 13.5 $nHm^2/Kg$ to 14.5 $nHm^2/Kg$ in an AC magnetic field of $f_{appl} \cdot H_{appl}$ of $1.8 \times 10^9$ $Am^{-1}s^{-1}$ ($f_{appl}$<120 kHz, $H_{appl}$<15.12 kA/m) or less.

6. The iron oxide nanoparticles according to claim 1, which generate heat sufficient to reach a temperature of at least 50° C. when placed in the biocompatible AC magnetic field.

7. A method of preparing iron oxide nanoparticles capable of heating in a biocompatible low AC magnetic field, the method comprising:

preparing iron oxide nanoparticles in which alkali metal or alkali earth metal is doped with $\gamma$-$Fe_2O_3$ by mixing an $Fe^{3+}$ precursor, an $M^+$ or $M^{2+}$ precursor where M is selected from the group consisting of Li, Na, K, Mg, and Ca, a surfactant, and a solvent in an oxygen atmosphere to form a mixture, and thermally decomposing the mixture at high temperature, wherein:

an Fe vacancy site of $\gamma$-$Fe_2O_3$ is doped with the alkali metal or alkali earth metal;

the iron oxide nanoparticles generate heat in a biocompatible AC magnetic field of $fa_{ppl} \cdot H_{appl}$ of $3.0 \times 10^9$ $Am^{-1}s^{-1}$ or less; and the iron oxide nanoparticles are represented by $M_{x-y}Fe_{2-x}O_3$, where M is selected from the group consisting of Li, Na, K, Mg, and Ca, and x satisfies 0.05<x<0.15, wherein the iron oxide nanoparticles are superparamagnetic.

8. The method according to claim 7, wherein the $Fe^{3+}$ precursor and the $M^+$ or $M^{2+}$ precursor comprises at least one member selected from the group consisting of metal nitrate, metal sulfate, metal acetylacetonate, metal fluoroacetoacetate, metal halide, metal perchlorate, metal alkyl oxide, metal sulfamate, metal stearate, and organic metal compounds.

9. The method according to claim 7, wherein the surfactant comprises at least one of organic acids with the chemical formula $C_nCOOH$ wherein 7<n<30.

10. The method according to claim 7, comprising:

(a) heating a mixed solution of an $Fe^{3+}$ precursor, an $M^+$ or $M^{2+}$ precursor where M is selected from the group consisting of Li, Na, K, Mg, and Ca, a surfactant, and a solvent to a temperature less than a boiling point of the solvent in a mixed atmosphere of oxygen and argon, followed by maintaining the mixed solution at the temperature for a certain period of time;

(b) heating the mixed solution again to the boiling point of the solvent in a mixed atmosphere of oxygen and argon, followed by maintaining the mixed solution at the boiling point for a certain period of time;

(c) removing a heat source and cooling the mixed solution to room temperature; and (d) performing precipitation and separation of nanoparticle powder by adding a polar solvent to the mixed solution and then performing centrifugation.

11. The method according to claim 7, wherein a doping level is adjusted by adjusting an amount of the $Fe^{3+}$ precursor or the $M^+$ or $M^{2+}$ precursor.

12. The method according to claim 7, wherein the iron oxide nanoparticles generate heat sufficient to reach a temperature of at least 50° C. when placed in the biocompatible AC magnetic field.

13. The method of claim 9, wherein at least one organic acid is selected from the group consisting of oleic acid, lauric acid, stearic acid, myristic acid, and hexadecanoic acid.

* * * * *

UNITED STATES PATENT AND TRADEMARK OFFICE
CERTIFICATE OF CORRECTION

PATENT NO. : 10,577,254 B2  
APPLICATION NO. : 15/788782  
DATED : March 3, 2020  
INVENTOR(S) : Seong Tae Bae and Jung Tak Jang It is certified that error appears in the above-identified patent and that said Letters Patent is hereby corrected as shown below:

In the Claims

In Claim 7 at Column 11, Line 30, the expression "fa$_{ppl}$·H$_{appl}$" should read -- f$_{appl}$·H$_{appl}$ --.

In Claim 7 at Column 11, Lines 32-33, the expression "M$_{x-y}$Fe$_{2-x}$O$_3$" should read -- M$_x$-γFe$_{2-x}$O$_3$ --.

Signed and Sealed this  
Seventh Day of April, 2020

Andrei Iancu  
*Director of the United States Patent and Trademark Office*